United States Patent [19]
Valducci

[11] Patent Number: 5,422,124
[45] Date of Patent: Jun. 6, 1995

[54] PHARMACEUTICAL ORAL CONTROLLED RELEASE COMPOSITION COMPRISING SMALL PELLETS OF BILE ACIDS

[75] Inventor: Roberto Valducci, Savignano sul Rubicone, Italy

[73] Assignee: Euderma S.r.l., Cerasolo di Coriano, Italy

[21] Appl. No.: 63,442

[22] Filed: May 18, 1993

[30] Foreign Application Priority Data

May 18, 1992 [IT] Italy .................. B092A0183

[51] Int. Cl.$^6$ ................. A61K 9/16
[52] U.S. Cl. .................. 424/497; 424/490; 424/499
[58] Field of Search .......... 424/528, 489, 490, 499, 424/501

[56] References Cited

U.S. PATENT DOCUMENTS

| | | | |
|---|---|---|---|
| 3,859,437 | 7/1975 | Weigand | 424/486 X |
| 4,185,099 | 1/1980 | Sorbini | 424/528 |
| 4,917,898 | 4/1990 | Angelico et al. | 424/528 |
| 5,091,192 | 2/1992 | See | 424/528 |

FOREIGN PATENT DOCUMENTS

| | | |
|---|---|---|
| 0273469 | 7/1988 | European Pat. Off. . |
| 0293751 | 12/1988 | European Pat. Off. . |
| 2152379 | 4/1973 | France .................. 424/528 |
| 2518880 | 7/1983 | France . |
| 2036558 | 7/1980 | United Kingdom ........ 424/528 |

*Primary Examiner*—Thurman K. Page
*Assistant Examiner*—P. Kulkosky
*Attorney, Agent, or Firm*—Dvorak and Traub

[57] ABSTRACT

A pharmaceutical oral controlled release composition comprising a multiplicity of microgranules or pellets, each of said pellets consisting of a core of active ingredient and binder and of a membrane applied upon said core, is described, wherein the active ingredient is a bile acid and the pellets have a particle-size of from 400 to 2000 microns.

6 Claims, No Drawings

PHARMACEUTICAL ORAL CONTROLLED RELEASE COMPOSITION COMPRISING SMALL PELLETS OF BILE ACIDS

BACKGROUND OF THE INVENTION

The present invention relates to a pharmaceutical oral composition for the controlled release of the active ingredient comprising a multiplicity of microgranules or small pellets, each consisting of a core of active ingredient and binder and of a membrane applied on said core of active ingredient, able to release said drug at successive times at a substantially regular rate. More particularly, the present invention relates to microgranules comprising a core containing bile acid and binder and thereon a membrane able to release the active ingredient at successive times at a substantially regular rate within the 12th hour starting from the time of administration, as well as a process for preparing the same.

As alkaline metal salts, the bile acids are compounds with a common steroid structure representing about 1% of mammals bile.

The bile acids are characterized by a) the presence of a side chain with 5 carbon atoms at C-17, the last of which bears an acid group, b) the presence of an hydroxylic group in C-3. The in nature occurring bile acids appear as derivatives conjugated with lysine or taurine and, in relation to the environment pH, as alkaline salts. Accordingly, they are also named sodium glycolates or taurocholates. In the human beings the bile acids are cholic, deoxycholic, chenodeoxycholic and respectively lithocholic acid. In bears' bile ursodeoxycholic acid was then found, that is the chenodeoxycholic acid epimer, whereas the 7-alpha-ketolithocholic acid was synthetically obtained. They arise chemically from cholanic acid, not occurring in nature but that can be obtained from cholesterol.

The bile acids are elaborated at liver level, starting from cholesterol, and are secreted by bile in the gut. They are partially destroyed by the enzimes of bacteric origin and mostly brought again to the liver by the vena cava (cycloenteroepatic). They are water soluble at the conjugated state. In phosphoric or sulfuric environment they are displaced from cholalic acid and impart a blue fluorescence to the medium, and with several aldehydes they yield colourings utilizable in quantitative analysis: the Pettenkofer's reaction with hydroxymethylfurfural produced by saccharose and the Charronat' reaction, in which vanilline is involved.

Moreover, the bile acids exhibit a softening activity, lower the surface tension in aqueous solvents, said phenomenon explaining the bile emulsive power and it s participation at the start of fats digestion, their attack being thus facilitated by means of the pancreatic secretion. This surface-active activity is inhibited by proteins.

Usually, the bile acids are not present in urine, except for the case of icterus, in which first biliary pigments can appear; they can be ascertained owing to their surface-active properties (the "sulphur flower" floats on a bile acids-containing liquid). In the blood, the bile acids rate (cholalemia) is very low, but in case of icterus it increases considerably. Cholalemia may be estimated by means of colorimetry or spectrometry of the above described reactions or by fluorometry. In therapy, biliary salts are employed (cholic and deoxycholic acid) in which bile is "depigmented": per oral route they act as cholagogues or as adjuvants in lipids digestion (chenodeoxycholic acid is a solvent for gall stones), whereas for rectal route they are administered as suppositories and in washings as mechanical laxatives owing to their ability to cause intestinal contractions. In the pharmaceutical industry they and bile play an important role in the manufacturing of steroidal hormones.

Since about twenty years, it is common practice to administer bile acids for denaturating lithogenous bile supersaturated with cholesterol and consequently for obtaining also the lysis of already formed cholesterol calculi. Said therapy should be continued for long periods of time, generally ranging from six months and two years.

Logically, this prolonged therapy is enormously facilitated by controlled release compositions permitting to administer daily to a patient only a unit dose form or two in particular cases.

Thus in IT-A-1.101.649 a pharmaceutical composition for oral use in the form of tablets is described, containing a bile acid as active principles in an amount of maximal 600–750 mg and adapted to lyse calculi of cholesterol origin. From these compositions the active principle can be released over a protracted time period. As bile acids, ursodeoxycholic chenodeoxycholic and 7-alpha-ketolithocholic acid are mentioned.

Now it is known that in comparison with tablets, compositions in the form of microgranules or pellets exhibit several advantages. In particular, hard gelatine capsules are filled with microgranules of active ingredient, and a few minutes after ingestion said capsule dissolves, thus permitting a complete releasing of the microgranules in the stomach and afterwards through the gastrointestinal tract and so removing the side effects and making easier the absorption in comparison with controlled release tablets (see for example Bechgaard H., Critical factors influencing gastrointestinal absorption—What is the role of pellets!, Acta Pharmaceutica Technologics, 28 (2) 1982, 149–156; Bechett A. H., Important formulation factors influencing drug absorption, Department of Pharmacy, Chelsea College, University of London; Wilson C. G. and Washington N., Assesment of disintegration and dissolution of dosage forms in vivo using gamma scintigraphy, Drug Development and Industrial Pharmacy, 14 (2 & 3), 211–281, 1988. Thus in US-A-2.918.411 a pharmaceutical composition for oral administration is described, comprising essentially a multiplicity of small pellets consisting of (a) polyvinylpyrrolidone, (b) a water soluble agent melting above 45° C. and selected from the group consisting of saturated fatty acids, saturated fatty acids esters of mono, di and tri-hydroxylated alcohols, mono and polyesters of saturated fatty acids, saturated aliphatic ketons and pharmaceutically acceptable sterols, and (c) a drug.

From BE-A-838.505 microcapsules able to release nitrogen to ruminants are known, wherein the active ingredient is coated with a paraffin and polyethylene film able to release the active ingredient within a predetermined period of time.

In US-A-4.572.833 a pharmaceutical oral controlled release composition is described, in which potassium chloride microgranules are coated with a membrane comprising a solvent, film-forming substance dissolved in the solvent and a hydrophobic substance microdispersed in film-forming mixture.

In FR-A-2.237.620 a depot galenic form for the oral administration of drugs is described, comprising spherical drug particles coated with a membrane consisting of (a) methylcellulose, ethylcellulose or propylcellulose, (b) a polymer of methacrylic acid and methacrylic acid esters (Eudragit L), cellulose phthalate, hydroxypropyl methylcellulose phthalate, lac, gum arabic, rosin, palmitic acid, myristic or stearic acid. Further patents describing pharmaceutical oral compositions comprising microgranules of active ingredient coated with a membrane able to release with the time said active ingredient are GB-A-1.413.186, GB-A-595.444 and FR-A-1.329.120.

In no one of the mentioned patents or in the above cited literature pharmaceutical oral compositions in the form of coated microgranules or pellets are described, containing bile acids as active ingredient.

Therefore, it was object of the present invention to provide pharmaceutical oral controlled release compositions comprising a multiplicity of microgranules or pellets each consisting of a core of active ingredient and binder and of a membrane able to release the drug at successive times at substantially regular rates. It was in particular object of the invention to provide a composition comprising microgranules coated with a particular membrane above to uniformly and uninterruptly release more than 500 microgranules per capsule in the gastrointestinal tract, thus enhancing absorption and in this way the pharmacological effect in comparison with the known tablets.

SUMMARY OF THE INVENTION

It has been found that if small pellets or microgranules each comprising a core of bile acid and binder are prepared, and a membrane comprising special polymers as used usually in this field is applied thereon, a composition can be obtained showing a well determined release with the time of the active ingredient.

Object of the present invention are thus pharmaceutical oral controlled release compositions comprising a multiplicity of small pellets or microgranules each consisting of a core of bile acid and binder and of a membrane applied on said core permitting the prolonged and controlled release of the drug in a well defined period time.

DESCRIPTION OF THE PREFERRED EMBODIMENTS

The new composition of the invention can be prepared according to known procedures, that is according to a process in which:
a) the bile acid is placed in a pan rotating at a speed of 5-15 rpm, a binder solution is added and the product thus obtained is subjected to a first sieving,
b) the first microgranules thus formed, having a particle size of 800-1400 microns, are re-worked in the pan under mild stirring, then they are dried until all the solvent is removed and again sieved, whereby other microgranules or cores are obtained having a prefixed diameter smaller than the diameter of the first microgranules,
c) said second microgranules, having a particle size of 300-1000 microns, are transferred again in the pan and, after wetting with the binder solution, further bile acid is added,
d) at last an ultimate sieving is accomplished, thus obtaining end-microgranules the size of which is as requested. Said microgranulesd are then coated with a membrane to give end-pellets having a particle-size of from 400 to 2000 microns and encapsulated.

As binder solution, a solution in 96% ethanol has been revealed to be particularly suitable, comprising from 0.5 to 5% of polyvinylpyrrolidone and from 2 to 10% of polysorbate 80. It is preferred a solution consisting of 2% polyvinylpyrrolidone and 6% polysorbate 80.

The end-product obtained according to the present invention is in the form of microgranules having the above mentioned particle-size and containing the bile acids at a very high concentration (active ingredient content from 100 to 550 mg). The end concentration is usually ranging from 95 to 97%, so that the high advantage is achieved to be able to fill the microgranules or pellets in 450 mg type "00" capsules, in 480 mg type "0 long" capsules, in 550 mg type "00" capsules and in 225 mg type "1" capsules. In a further embodiment of the present invention, the composition can be also in the form of monodose bag or multidose granulate.

EXAMPLE

In a stainless steel rotary pan, rotating at a speed of from 10 to 20 rpm, 67.5 kg ursodeoxycholic acid were placed, then 5 kg of the binder solution were added (polyvinylpyrrolidone and polysorbate solution in ethanol) and the pan was rotated for 10-25 minutes.

The product thus obtained was then transferred in a granulator equipped with screen having a net gap of 800-1400 microns, and these first microgranules were replaced in the pan rotating again at 10-25 rpm.

The microgranules were then dried in a thermostatated box at 30° C. for 10-20 hours until a complete evaporation of the alcohol was reached. The granulate thus obtained was sieved again, thus separating a fraction of 300-1000 microns constituting the second microgranules. Said fraction was placed again in the pan and thereon, by means of a high pressure pump, a further binder solution and further ursodeoxycholic acid were applied.

The end-microgranules were again sieved. They were transferred in the pan and, always by means of a high pressure pump, at 10-15 minutes intervals the membrane was applied with talc addings to give end-pellets having diameters of from 400 to 2000 microns. The membrane comprised 5 kg of an acetone solution containing 0.875 kg methacrylic acid esters (Eudragit L, trade mark of Rohm-Pharma). The end composition of the product thus obtained read as follows:

| ursodeoxycholic acid | 96.77% |
|---|---|
| polyvinylpyrrolidone | 0.39% |
| polysorbate 80 | 1.33% |
| Eudragit L | 1.26% |
| talc | 0.25% |

Solvents alcohol and acetone, employed in the preparation, are not reported in the composition being evaporated during the process. Even though the example has been described referring to ursodeoxycholic acid only, it is clear that other bile acids can be used, thus obtaining the same results.

What is claimed is:
1. A pharmaceutical oral controlled release composition comprising a multiplicity of small individual, substantially identical, pellets, each pellet having a core of medicament in admixture with a binder and a single coating membrane applied thereon, said coating membrane being a mixture of a methacrylic acid copolymer and talc, and said binder being a mixture of polyvinyl- pyrrolidone and polysorbate 80, characterized in that the medicament is selected from the group consisting of ursodeoxycholic acid, chenodeoxycholic acid and 7-alpha-ketolytocholic acid, the membrane being present in an amount of approximately 1.51% and the binder being present in an amount of approximately 1.7%, based on the composition total weight respectively, and in that the medicament concentration is from approximately 95 to 97%, wherein the medicament is released at a substantially regular rate.

2. A pharmaceutical composition according to claim 1, wherein each pellet has a size of from 400 to 2000 micron.

3. A pharmaceutical composition according to claim 1, wherein the binder comprises 0.39% of polyvinylpyrrolidone and 1.33% of polysorbate 80.

4. A pharmaceutical composition according to claim 1, wherein the membrane comprises approximately 1.26% of a methacrylic acid copolymer and approximately 0.25% of talc.

5. A process for preparing a pharmaceutical oral controlled release composition according to claim 1, comprising steps of coating microgranules of medicament and binder with a membrane, wherein the medicament is selected from the group consisting of ursodeoxycholic acid, chenodeoxycholic acid and 7-alpha-ketolytocholic acid, the binder is a mixture of polyvinylpyrrolidone and polysorbate 80, and the coating membrane is a mixture of a methacrylic acid copolymer and talc.

6. The processing according to claim 5, wherein the coating membrane is applied from a solution containing both the components methacrylic acid esters and talc.

* * * * *